United States Patent [19]
Fitterer et al.

[11] 3,935,079
[45] Jan. 27, 1976

[54] METHOD AND APPARATUS FOR DISPLAYING ACTIVE OXYGEN AND SENSOR TEMPERATURE

[75] Inventors: Charles E. Fitterer, Allison Park; Carl D. Cassler, Pittsburgh, both of Pa.

[73] Assignee: Fitterer Engineering Associates, Inc., Oakmont, Pa.

[22] Filed: Nov. 3, 1972

[21] Appl. No.: 303,370

[52] U.S. Cl. ............. 346/45; 340/213 Q; 340/421
[51] Int. Cl.² ................. G01N 27/46; G08B 29/00
[58] Field of Search ............ 204/1 T, 195 S, 1 S; 340/213 R, 213 Q, 253 R, 421, 152 T, 236, 324 R, 324 A

[56] References Cited
UNITED STATES PATENTS

| | | | |
|---|---|---|---|
| 3,474,438 | 10/1969 | Lauher | 340/324 A |
| 3,619,381 | 11/1971 | Fitterer | 204/1 T |
| 3,652,427 | 3/1972 | Flood et al. | 204/195 S |
| 3,723,279 | 3/1973 | Fruehan et al. | 204/195 S |
| 3,758,397 | 9/1973 | Rittiger et al. | 204/195 S |

*Primary Examiner*—T. Tung
*Attorney, Agent, or Firm*—Lane, Aitken, Dunner & Ziems

[57] ABSTRACT

A method and apparatus for displaying the active oxygen content of a liquid metal and the sensor temperature of a probe from signals developed by the probe which is capable of being plunged directly into the liquid metal. The probe comprises a small mass of solid oxygen-permeable electrolyte in the end of a refractory insulating tube, an oxygen reference material in contact with the inner surface of the electrolyte, and suitable electrodes for providing both a signal representative of the active oxygen of the liquid metal and a signal representative of the sensor temperature. The apparatus comprises first recording means for displaying the sensor temperature, and second recording means for displaying the active oxygen of the metal, a source of power, and sequencing means which are initially responsive to the probe emf for sequencing the operation of the apparatus. The method and sequence of steps in connection with displaying the sensor temperature and the active oxygen on the instrument and the determination of the active oxygen on the liquid metal therefrom are also disclosed. The apparatus is portable, self-contained and operable from either a conventional a-c source or rechargeable batteries to provide a sequence of signals to the operator to advise that the probe is operative and properly connected, that the apparatus is ready to receive signals from the probe, that the signals are being received, and that the sequence is complete so that the probe may be removed from the liquid metal.

19 Claims, 8 Drawing Figures

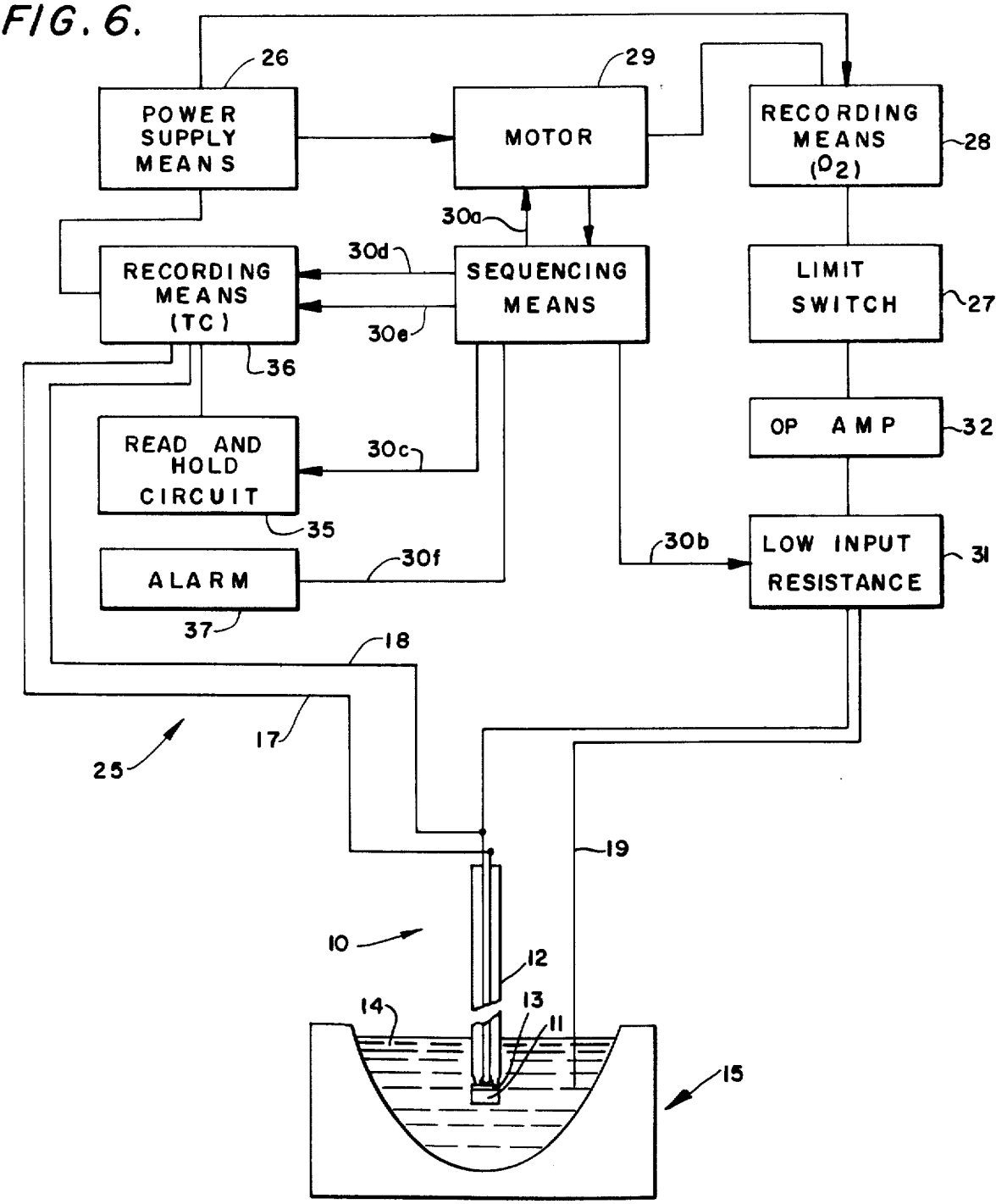

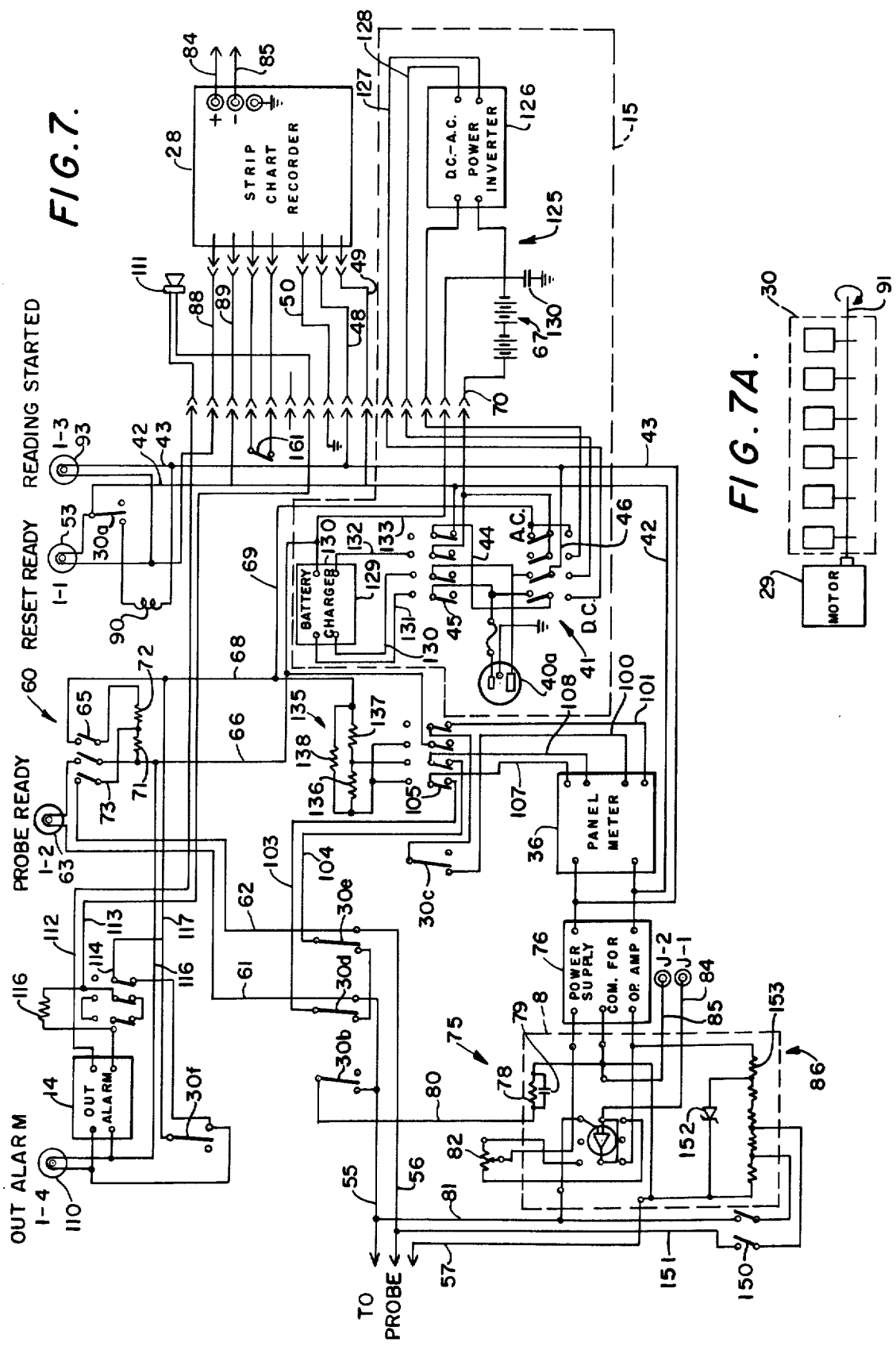

METHOD AND APPARATUS FOR DISPLAYING ACTIVE OXYGEN AND SENSOR TEMPERATURE

BACKGROUND OF THE INVENTION

This invention relates to an apparatus which may be used in the control of the quality of liquid metals, for example, liquid steel or copper, in commercial production. More particularly, this invention relates to an apparatus for displaying the active oxygen content of a liquid metal and the sensor temperature developed by an oxygen sensing probe immersed in the liquid metal. Still more particularly, this invention relates to a method and apparatus for displaying such data.

The advent of new and rapid processes for the refining of liquid steel, such as the basic oxygen furnace, has emphasized the need for extremely rapid methods of analyses of the metal while the metal is still liquid in the furnace or in the ladle. Earlier steel refining processes, such as the basic open hearth, required upward to ten hours or more to refine completely a heat of 200 or 300 tons from melt-down to tap, whereas the same amount of steel is now being processed in the basic oxygen furnace in as little as thirty minutes. As a result, an open hearth operator had as much as an hour in the latter part of the heat in which to obtain sufficient analytical data to make decisions regarding the types and quantities of the final additions to be made, to make the additions, and then to tap the heat within the desired specifications. Today, the refining reactions occur so rapidly in the basic oxygen furnace that the operator has only about five minutes in which to obtain his analytical data and in which to make the necessary additions prior to tapping. Sometimes this final stage of the heat is reduced to as little as one or two minutes.

Thus, the need for very rapid analytical methods in modern steel-making is apparent. Such data must be available instantaneously and provide the necessary information in a matter of seconds.

In most steels, the data needed for such control are the temperature, the amount of carbon and the active oxygen which are present. The immersion thermocouples which have been in use for some 20 or 30 years will indicate the temperature of liquid steel in about 10 seconds. In addition, rapid methods for the determination of the carbon content have been available for the past several years.

However, the determination of the active of the dissolved oxygen in liquid metals was not possible until the invention of the solid oxygen-ion electrolyte sensor or probe which is capable of being plunged directly into the liquid metal. Such a device is described in the literature of the following articles, for example:

1. G. R. Fitterer, "Progress in the Development of a Device for the Direct Determination of Oxygen in Liquid Steel", AIME, J. Metals, August 1966; and 2. G. R. Fitterer, "Measuring the Active Oxygen Content in Commercial Steel," Instrument Society of America, "Iron and Steel Instrumentation Symposium", March 1970, Pittsburgh, Pa.

This device is also disclosed in detail in U.S. Pat. to G. R. Fitterer, No. 3,619,381, issued Nov. 9, 1971.

Fortunately, this device also responds very rapidly so that the oxygen content of the liquid metal is indicated within fifteen to twenty seconds. With this information, the steel melter can decide about the amount and types of deoxidizing alloys to add so as to insure that the desired degree of soundness and other qualities are provided when the metal solidifies as an ingot, as a casting, or during the continuous casting process. Thus, the three most important items of information needed by the steel melter in all of the steelmaking processes are available to him within seconds for the first time in history.

Accordingly, it is an object of this invention to provide a method and appratus for displaying such data for the convenience of their users. It is generally desired that such an apparatus be portable so that it may be carried by the operator to different stations in the plant or situated permanently at one station as desired.

Because of the constraints on this invention and its environment, it is also desired that the apparatus be completely self-contained so that it may be operated on rechargeable batteries or on line current as desired.

In addition, it is desired that such an apparatus provide a completely automatic sequence of events so that only one operator is needed to make the oxygen determination.

Thus, it is a principal object of this invention to provide such a method and apparatus described above.

BRIEF SUMMARY OF THE INVENTION

The apparatus according to this invention is portable, self-contained, and comprises a source of power which may be developed from a conventional a-c source, or from batteries, and further includes means for recharging the batteries and testing the operative conditions of the batteries to determine whether recharging is necessary. A first recording means, including a read and hold circuit, is provided for displaying sensor temperature and a second recording means is provided for displaying active oxygen. The apparatus is operable with any source of voltage signals representing sensor temperature, and active oxygen, but is particularly adapted for use with the output of a sensor which generally comprises a small mass of solid, oxygen-permeable electrolyte, such as calcia-stabilized zirconia, in the end of a refractory insulating tube, and having an oxygen reference material in contact with the inner surface of the electrolyte. A plurality of electrodes are provided in contact with the electrolyte to provide the signals representative of the temperature and the difference in oxygen pressure on each side of the electrolyte which can thus be correlated with the oxygen content of the metal and with the temperature of the sensor. Means are provided in the apparatus to initiate the sequence of events to display such readings from the emf of the sensor shortly after the insertion of the probe into the liquid metal. A plurality of lamps are provided to apprise the operator that the apparatus is ready for use, and that the probe or sensor is properly secured and in circuit with the apparatus. One lamp indicates that the apparatus is ready for use, another indicates that the readings have started, still another indicates that the probe is operative and properly connected, while yet another lamp and an audible warning signal inform the operator that the readings have been completed and that he may remove the probe from the metal. It is a feature of the invention that the thermocouple indication is retained on the first recording means at least until the next probe is inserted into the circuit, thus giving the operator sufficient time to record the temperature. Still further, means are provided to calibrate the recorder for muting or testing the alarm and for charging the batteries when necessary.

Sequencing means, comprising a motor connected to a shaft for predeterminedly camming a plurality of switches, are provided to sequence the operation of the apparatus and are initially responsive to the signals from the probe. The apparatus, thus programmed by the sequencing means, performs a plurality of steps to achieve its objectives.

The method according to the invention comprises the steps of providing a probe of the type indicated, securing the probe in circuit with the input of the apparatus, testing to determine that the probe is properly in circuit with the input of the apparatus and operable, sensing a predetermined level of signals from the sensor, recording the sensor emf and initiating the operation of the sequencing means. During the operation of the apparatus, a low input impedance across an operational amplifier in circuit with the input signals is disconnected at about two or three seconds after the start of the cycle and at about the same time the read and hold circuit of the first recording means is disconnected to cause the first recording means to seek and hold a zero setting until the next impulse is received during the sequence. At about fifteen seconds after the start of the cycle, the thermocouple leads from the probe are connected to the first recording means and the thermocouple emf or temperature of the liquid metal is indicated on the first recording means. At about nineteen seconds after the sequence is initiated, a closed or short circuit is placed across the read and hold circuit and the temperature indication is retained on the first recording means. During the sequencing, the signals representing the oxygen content of the liquid metal are displayed and/or recorded on the second recording means. At about 20 seconds after the start of the cycle, a warning signal is actuated and thereafter terminated to apprise the operator that the probe may be removed from the metal. After about 60 seconds after the start of the cycle, the entire circuit of the apparatus is restored to its original starting state and the temperature indication is retained on the first recording means at least until the start of the next cycle.

Various additional features and capabilities of the apparatus of the invention are discussed in detail hereinafter.

These and other objects and features of the invention will become apparent from a review of the accompanying written description of the invention together with the review of the accompanying drawings.

BRIEF DESCRIPTION OF THE DRAWINGS

In the drawings:

FIG. 6 is a schematic illustration, in block form, of a circuit according to the invention in combination with the oxygen sensing probe;

FIG. 7 is a detailed schematic drawing of the circuit according to the invention; and FIG. 7A is a schematic illustration of the sequential operation of the respective switches by a motor.

DETAILED DESCRIPTION OF THE PREFERRED EMBODIMENT

Figure 1:
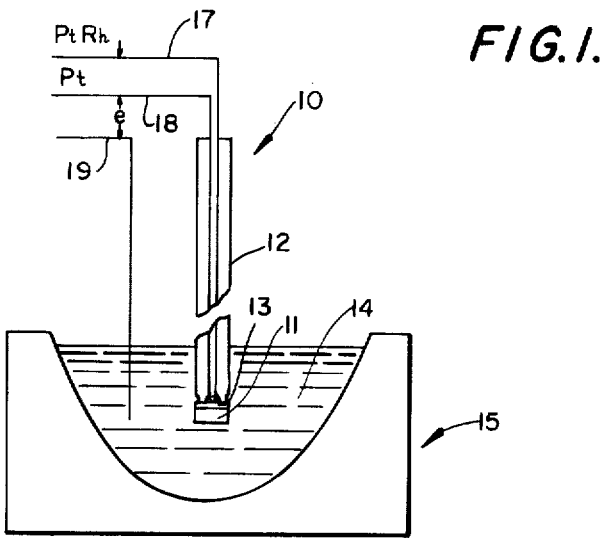
FIG. 1 is a schematic representation of a thermal shock resistant oxygen sensing probe immersed in a bath of liquid metal.

In FIG. 1, the solid electrolyte sensor with which the circuit according to the invention is preferably used is designated generally by the reference numeral 10 and comprises a small mass of solid oxygen-permeable electrolyte 11, such as calcia-stabilized zirconia, in the end of a refractory insulating tube 12.

A reference material 13, such as Mo—MoO is in contact with the inner surface of the electrolyte while the outer surface of the electrolyte is in contact with the bath of liquid steel, retained in an apparatus designated generally by the reference numeral 15, such as a basic oxygen furnace, an open hearth, a ladle, and the like. A plurality of electrodes 17, 18 and 19 are operatively connected to the probe 10 in such a manner that a temperature reading may be determined from the potential in millivolts which exists between lead 17, for example a PtRh lead, and lead 18, for example a Pt lead. An emf in millivolts is also derived between the lead 18 and the lead 19 representing a voltage which can be correlated with the oxygen content of the metal 14.

When the sensor 10 is plunged into the liquid metal 14 containing the active or dissolved oxygen, the difference in oxygen pressure on the opposed sides of the electrolyte 11 provides the signal which can be correlated with the dissolved oxygen content of the metal. The reference material 13 provides a known oxygen pressure inside the sensor for comparison with the unkown oxygen pressure of that dissolved in the liquid metal 14. This relation is illustrated by the equation:

$$E = \frac{RT}{nF} \ln \frac{p_{O_2}}{p^*_{O_2}}$$

wherein  E is the sensor voltage;
R is the gas constant;
F is the Faraday equivalent;
n is the valence equivalent depending upon the reference material being used;
ln is the natural logarithm;
$p_{O_2}$ is the partial pressure of the oxygen in the liquid metal; and
$p^*_{O_2}$ is the partial pressure of oxygen developed by the reference material at the temperature of the test.

From this equation, it may be seen that such oxygen sensors are quite temperature sensitive to the extent that it is imperative that the temperature of the sensor be known at the time the oxygen probe reading is being made. Further details of such an oxygen sensing probe are contained in United States Patent No. 3,619,381, in the name of Dr. G. R. Fitterer, issued November 9, 1971, the disclosure of which is herein incorporated by reference.

The oxygen sensors which are described in the literature cited above and in the above-mentioned patent contain their own thermocouples corresponding to leads 17 and 18 of FIG. 1 and the circuit of this invention is capable of measuring both the temperature and the emf from the oxygen sensor simultaneously.

Figure 2:
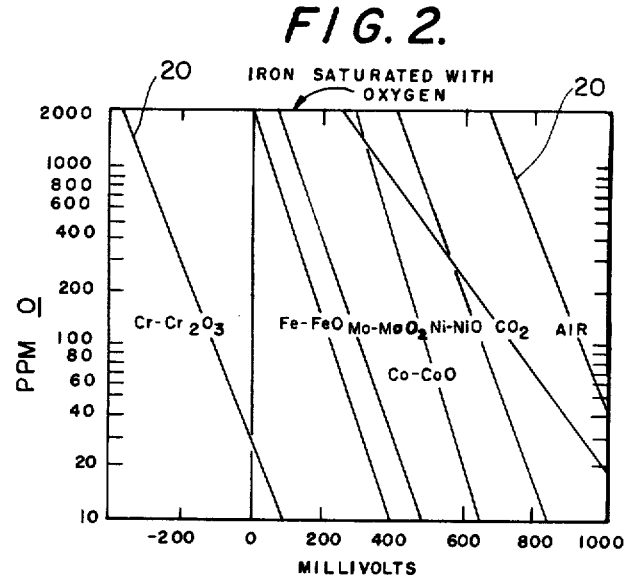
FIG. 2 is a graph of calculated oxygen sensing probe potentials using various standard references at 2900 F.

FIG. 2 illustrates the relationship of the sensor emf on leads 18 and 19 with the oxygen content of the liquid metal 14 at a temperature of 2900°F. when various reference materials 13 are used in the probe 10. From this figure, it may be seen that an emf, in millivolts as shown, and plotted on the abscissa can be converted to the dissolved oxygen content of the metal in parts per million, plotted on the ordinate, for the particular reference material used, as indicated by one of the plurality of lines 20.

Figure 3:
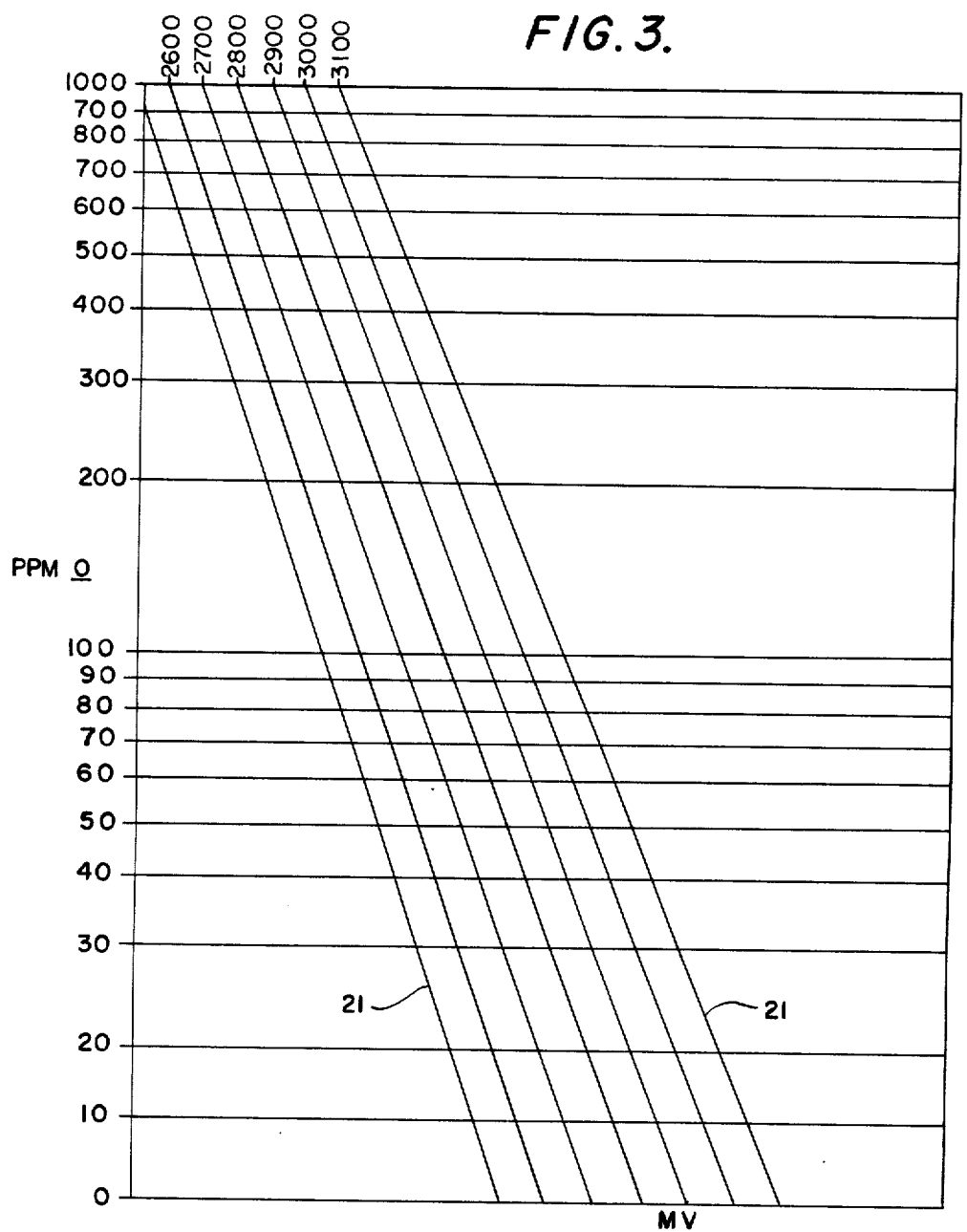
FIG. 3 is a conversion graph for converting the millivolt readings from the oxygen sensing probe to parts per million of dissolved oxygen in the metal as a function of temperature for a sensor using a mixture of molybdenum and its oxide as the oxygen reference material.

FIG. 3 is a graph to convert the emf reading on leads 18 and 19 from the probe 10 to the dissolved oxygen content in parts per million in the metal 14, as a function of temperature. This representative graph is applicable when a mixture of molybdenum and its oxide is used as the oxygen reference material 13 in the sensor 10. Similar graphs can be developed for other reference materials in the same manner. The emf reading is plotted on the abscissa while the oxygen content is plotted on the ordinate, while various temperatures are indicated by the lines 21.

Figure 4:
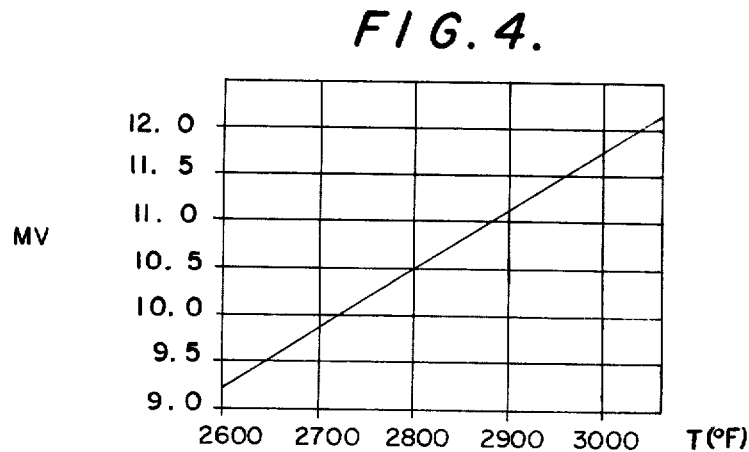
FIG. 4 is a graph relating to the millivolt readings from the thermocouple on the probe to the sensor temperature for a type B thermocouple.

FIG. 4 is a graph of the sensor temperature in degrees Fahrenheit plotted on the abscissa and the millivolt reading on leads 17 and 18 from the sensor 10 plotted on the ordinate. Thus, by knowing the emf reading on leads 17 and 18, the sensor temperature may be determined for use with the chart of FIG. 3 to convert the emf reading on leads 18 and 19 to the dissolved oxygen content of the metal. Thus, the information in FIGS. 3 and 4 is provided as evidence that the oxygen content of liquid metal, such as steel, may be determined from the emf of the sensor and the corresponding temperature at the time of the reading. Such graphs have been used to make the calculations by first determining the sensor temperature from the millivolt reading according to the graph of FIG. 4, and using the appropriate temperature line of the graph of FIG. 3 to convert the millivolt readings at that particular temperature to the dissolved oxygen content of the metals as a function of the temperature.

Figure 5:
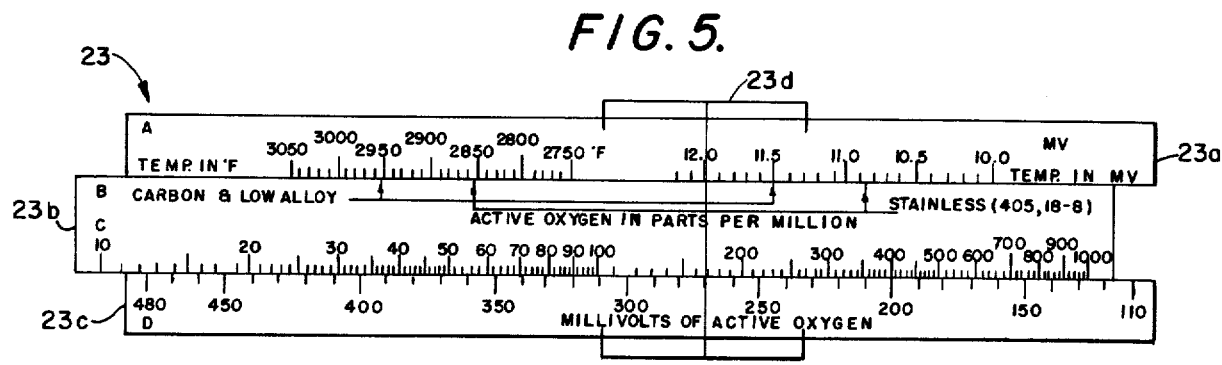
FIG. 5 is an illustration of a slide rule for calculating the temperature of and the dissolved oxygen content of liquid steel from the readings from a solid electrolyte sensor using the Mo—MoO as the standard oxygen reference material.

FIG. 5 illustrates a slide rule indicated generally by the reference numeral 23 for converting the millivolt representation of the temperature on the thermocouple in the sensor on the righthand portion of the upper fixed portion 23a of the slide rule to a temperature in degrees Fahrenheit indicated by indicia in the upper left portion of the slide rule by sliding the central portion 23b of the slide rule to align the righthand arrow with the mv reading and following the indicia thereon (for indicating for carbon and low alloy steels with one set of arrows in comparison to stainless steel in the other set of arrows) to the corresponding temperature aligned with the lefthand arrow. After the slideable portion 23b has been fixed by the conversion of the millivolt readings to temperature, the active oxygen in parts per million may be directly determined by moving the slideable member 23d along the lower portion of the slide rule 23c having indicia representing the millivolts of active oxygen to determine directly on the lower portion of the slideable portion 23b the active oxygen content in parts per million. This particular slide rule has been developed using $Mo—MoO_2$ as a standard oxygen reference material, but a similar instrument can be developed for other reference materials. As may be seen, in using the oxygen sensing probe in field conditions, the slide rule according to FIG. 5 has materially enhanced the speed at which such calculations may be made by the operator.

FIG. 6 is a block diagram of the circuit according to the invention, designated generally by the reference numeral 25, in combination with the diagrammatic illustration of the probe 10 immersed in the liquid metal 14, as shown in FIG. 1. The apparatus 25 according to the invention has certain basic characteristics which are essential to utilizing effectively the output of sensors of this type. It is contemplated that the apparatus 25 is portable so that it may be carried by the operator to different stations in the plant or may be situated permanently at one station if desired. The apparatus 25 is also completely self-contained so that it may be operated on rechargeable batteries or on line current.

In one embodiment of the invention, a potentiometric chart recorder provided with a high input impedance is used to record the emf from the sensor 10 and a digital panel meter is used to indicate the emf from the thermocouple or to indicate the temperature directly. Two panel meters could be used, as well as two recorders, or a two channel recorder, if preferred.

It is a characteristic of the present invention that a sequence of events is initiated from the emf of the sensor within seconds after the insertion of the probe 10 into the liquid metal 14. First, the chart mechanism of the recorder is actuated from the sensor emf and the recording of that emf is begun within a few seconds after the immersion of the probe 10 into the liquid metal 14. At about the same time, the digital panel meter first exhibits a zero reading and then indicates a thermocouple emf or the temperature directly as desired. Since the thermocouple emf reaches a steady value after about ten seconds and since the sensor obtains a steady emf after about fifteen seconds, a warning signal thereafter informs the operator that the reading has been completed and that he may remove the probe from the metal. Meanwhile, the thermocouple indication is retained on the digital meter on the face of the instrument until the next probe is inserted into the circuit giving the operator ample time to record the temperature.

The oxygen content of the metal may then be determined by referring these values to the calibration charts as shown in FIGS. 3 and 4 or with the help of the slide rule which has been shown in FIG. 5. An alternative procedure would be to provide both readings into a device such as an analogue digital computer in which the digital panel meter as described above could also become a part of the computer.

When a new sensor or probe 10 is plugged into the circuit by attachment to a handle adapted to receive such probes, and the probe is immersed into the liquid metal, the complete sequence of events is automatically repeated with a new set of data depending upon the analysis and temperature. Because of the portability of the apparatus, its complete independence electrically from the regular power supply and in particular its completely automatic sequence of circuit changes, only one operator is needed to make the oxygen determination. Furthermore, his only function is to plug a sensor into the handle, turn on the main power switch, insert the probe into the liquid metal, and calculate the oxygen content from the instrument records on the calibration chart or the calculator as mentioned above. Thereafter, he need only insert a new probe into the handle in order to start the sequence over again.

The sequence of events which are characteristic of the apparatus of this invention are best described generally by reference to the schematic of the circuit in block diagram as illustrated in FIG. 6. In this embodiment of the apparatus, two sets of events occur simultaneously upon the insertion of a sensor into the liquid metal. The first set involves automatic recording of the sensor emf, and the other set of events is a thermocouple indication of the temperature. The various steps in the sequence using the apparatus in FIG. 6 are as follows.

First, the power supply 26 is turned on.

Second, the probe 10 is inserted into a suitable handle (not shown) and the sensor 10 is plunged into the liquid metal 14.

Third, as the probe emf developes, it actuates a limit switch 27 which can be external to or a component part of the recorder.

Fourth, the chart drive of the recorder 28 starts operating and a record of the sensor emf is recorded through contact with the sensor leads 18 and 19. At this time, a synchronous motor 29 which drives a multi-gang timer having six cam-operated switches 30a through 30f starts to rotate and the auxiliary switch 30a connects the motor circuit to the motor to insure a power supply thereto.

Fifth, within two or three seconds, a switch 30b disconnects the low input impedance 31 from across the operational amplifier 32 thus insuring a high input impedance which is required in the sensor circuit.

Sixth, and at about the same time as the fifth step above, the switch 30c disconnects the read and hold circuit 35, thus causing the digital panel meter 36 to seek and hold a zero setting until the next programmed impulse is received from the timer switch 30 to permit the displaying of the emf representing the temperature of the probe.

Seventh, the switches 30d and 30e connect the thermocouple leads 17 and 18 to the digital panel meter 36 and either the thermocouple emf or the temperature of the liquid metal directly is indicated on the panel. When the temperature of the liquid metal is diplayed directly on the face of the meter, the location of the indicia thereon is such that the conversion discussed in connection with FIG. 4 has been performed.

Eighth, at about nineteen seconds after start, a short is placed across the read and hold circuit 35 (which may be part of the digital panel meter 36) by the switch 30c and the temperature indication is locked in on the digital panel, thus permitting the operator to make a note of the temperature on the record.

Ninth, at about twenty seconds after start, a switch 30f actuates the warning signal from a suitable signaling means 37 which is subsequently turned off by the same switch at about 25 seconds after the start of the cycle, thus providing a warning period of about 5 seconds for the operator to remove the probe from the metal.

Tenth, after about 60 seconds, the entire circuit is restored to the original or starting position by switch 30a. However, the temperature indication is retained on the digital panel meter 36 until the sixth step as described above with a new probe. At that time, the panel meter 36 again indicates a zero setting during a new cycle as previously described.

Thus, it is apparent that the apparatus is completely automatic and permits the operator complete freedom from the need to make instrument adjustments. The data is thus available to the operator within about 30 seconds and the readings may be repeated, if necessary or if desirable about every minute. All that is required of the operator is to turn on the power, plug in a new probe and insert the probe into the liquid metal. The operator can then remove the used probe, make notes regarding the results indicating the calculation of the parts per million of oxygen, and if he wishes he may immediately insert a new probe into the metal without any contact with the apparatus which will proceed through a new cycle automatically. Thus, use of the instrument 25 saves costly labor charges, as well as being extremely convenient. Moreover, the instrument is extremely accurate, displaying oxygen content within a tolerance on the order of about ± 10% of the amount present in parts per million and a sensor temperature with an accuracy on the order of about ± 5°F.

A detailed schematic and wiring diagram of the apparatus according to the invention is shown in FIG. 7 wherein a number of additional features of the invention are indicated. Among these is a battery circuit which renders the apparatus completely independent of the usual a-c power lines which are sometimes quite unreliable and variable and often inaccessible in steel plants. This battery circuit includes gel-cell type batteries which are connected to a vibrator system which converts the direct current to 110 volts a-c. In addition, a battery charger is included together with a test circuit for indicating whether the batteries require recharging under a simulated load condition. For example, it is contemplated that the batteries are capable of supplying considerable current to operate the apparatus for upward to one and one-half or two hours continuously without recharging. Since the use cycles are only of one minute duration, the apparatus may be used for a considerable number of test without the need for recharging, another significant factor in the field use of the device.

The apparatus according to the invention also has a system of sequencing lights, each of which will indicate that a certain step in the cycle has been successfully attained. For example, in one embodiment of the invention, four such lights are used. A white light, or "reset ready" light, indicates that the circuit is ready for the start of the cycle; a green light, or "probe ready" light, provides an indication of the continuity of the thermocouple circuit; a yellow light, or "reading started" light, indicates that the timer motor is running; and a red, perhaps blinking light, or "out alarm" light, is synchronized with the alarm system which indicates to the operator that the reading has been made and that he can remove the sensor from the liquid metal. After about 60 seconds, when the circuit returns to its original position, the "reset ready" light again is displayed.

Turning now to a detailed discussion of FIG. 7, the elements of FIG. 7 which correspond to those previously described are identified with like reference numerals.

The power supply, designated generally in phantom outline by the reference numeral 15, comprises a plug 40 connected to a suitable recepticle 40a and is applied to the circuit by the closure of switch 41. The switch 41 is preferably a three-position switch having an a-c position (as shown), a d-c position and an off position. The closure of the switch 41 provides power for the circuit on leads 42 and 43 by way of the lead 44, connected to a terminal of the switch 45, and by a lead 46. This energizes the panel meter 36 which, by way of example, may be an API Model 4304 Digital Panel Meter. The power is also supplied to the strip chart recorder 28 by way of leads 48 and 49. For example, the strip chart recorder 28 may be a Hewlett-Packard, Model 680, equipped with an internal limit actuating circuit and a remote chart drive circuit. The lead 50 from the strip chart recorder is connected to ground. Because the switch 30a is in a normally open position, the "reset ready" lamp 53 is thus energized by the power on the leads 88 and 89, indicating that the circuit is ready for operation. The switches 30a– 30f are operated in sequence by the motor 29 as indicated by FIG. 7A.

When the probe 10 is inserted in the handle, the leads 55, 56 and 57 are connected to the leads 17, 18 and 19 of the probe 10 so that a thermocouple reading is available from the emf which exists between the leads 55 and 56, while the oxygen reading is available from the emf which exists between the leads 55 and 57.

The signal on the leads 55 and 56 is provided to a "probe ready" circuit designated generally by the reference numeral 60 by way of leads 61 and 62 respectively. A "probe ready" lamp 63 is in series with the lead 61 and with the switch 65. The switch 65 is normally open and is momentarily depressed to obtain an indication on the lamp 63. The switch 65 is connected by way of the lead 66 to the negative side of the batteries 67 while another terminal of the switch 65 is connected by way of leads 68 and 69 through a terminal of the switch 41 and a lead 70 to a positive side of the batteries 67. These connections apply the battery potential to the voltage divider circuit comprising resistors 71 and 72, which are respectively about 20 ohms and 100 ohms to protect the thermocouple circuit on the probe from damage when depressing the switch 65 to determine whether the probe is ready to operate. The common connection between the resistors 71 and 72 is connected by a lead 73 to the lead 62 to complete the "probe ready" test circuit. Thus, by depressing the switch 65 momentarily from its normally open position, the operability of the thermocouple circuit which exists between leads 55 and 56 can be immediately determined. When the probe is in the operative state, the test may be continued, while if the depression of the switch 65 fails to indicate that the probe is in an operative condition, the probe should be changed on the handle.

Input circuit means designated generally by the reference numeral 75 comprise an operational amplifier (op amp) designated in phantom outline by the reference numeral 8, the power to which is provided by a power supply for the operational amplifier, designated by the reference numeral 76. As specific examples, the operational amplifier may be a Model TP 1420 and the power supply a Model TP 2204, both available from Teledyne-Philbrick. The lead 85 is a common lead connected to the input lead 57 and to the common lead of the power supply.

The signal on the lead 55 is provided through a switch 30b through the low input resistors 78 in parallel with capacitor 79. The signal on the lead 55 is also provided by way of a lead 81 to an input terminal of the amplifier. A variable resistor 82 is connected across the amplifier to provide a zero off-set adjustment for the operational amplifier. The resistor 82 is on the order of 10 K ohms. The output from the amplifier is provided on a lead 84 while the common output is provided on a lead 85, which leads are connected to the input of the strip chart recorder 28.

The operational amplifier 8 acts as a buffer or isolator between the recording circuit according to the invention and the probe 10 to prevent loading on the probe and distortion of the output signals therefrom. The input circuit means 75 also comprise a signal calibration circuit designated generally by the reference numeral 86 which will be discussed hereinafter.

The recorder 28 is provided with an internal limit switch circuit such that the strip chart on the recorder begins to operate when the probe potential from the amplifier 8 on leads 84 and 85 is on the order of 50 millivolts. The trip point on the limit switch circuit may be adjustable.

When the potential provided to the recorder is sufficient to actuate the limit circuit in the recorder, the line potential is provided on leads 88 and 89 from the recorder to the series circuit comprising the reset ready lamp 53 and the energizing winding 90 of the motor 29. The motor 29, as indicated in FIG. 7A, drives a shaft 91 which sequentially actuates the plurality of switches 30a through 30f by operation of cams on the shaft. The contact of the switches 30a-30f throughout the drawings are correspondingly labeled. The mechanical sequencing circuit could also be replaced by an electrical circuit having electronic switches.

When the motor winding 90 has been energized by the presence of a potential on leads 88 and 89, the motor begins to rotate the shaft 91 causing the closure of the switch 30a to provide power from leads 42 and 43 directly to the motor winding 90 by by-passing the reset ready lamp 53. Thus, the lamp 53 is extinguished, while closure of the switch 30a causes the "readings started" lamp 93 to illuminate, apprising the operator that the readings are under way.

Further rotation of the motor 29 and the shaft 91 causes the switch 30b in circuit with the lead 55 to open to disconnect the resistor 78, on the order of 500 K ohms, from the input circuit. The resistor 78 is connected in the circuit to prevent the amplifier 8 from being open-circuited so that after a signal is available from the probe to be received at the input of the amplifier, the low input resistor 78 is disconnected from the input circuit, permitting the probe to see an input impedance on the order of $10^{12}$ ohms which is the high input impedance of the amplifier 8. The opening of the switch 30a occurs within about two or three seconds after the start of the cycle to disconnect the input resistor 78.

At about the same time, the switch 30c opens to disconnect a read and hold circuit in the panel meter 36 by opening the circuit between leads 100 and 101. The read and hold circuit is built into the digital panel meter 36. This will cause the digital panel meter 36 to seek and hold a zero setting until the next impulse is received from the circuit as a result of the programmed sequence.

At about 15 seconds after the start of the cycle, the time at which the thermocouple emf is generally stable, the switches 30d and 30e close to cause the signals on the thermocouple sensing leads 55 and 56 to be provided on the leads 103 and 104 through a switch 105 to the digital panel meter 36, thus providing an input on the leads 107 and 108 to the meter 36. Thus, at this point in the cycle, either the thermocouple emf or the temperature of the liquid metal is directly indicated on the panel of the meter 36.

At about nineteen seconds after the start of the cycle, a short is placed across the read and hold circuit of the digital panel meter by the return of the switch 30c to its starting position, effectively placing a short across the leads 100 and 101. This causes the temperature indication to be locked in on the digital panel for future reference.

At about 20 seconds after the start of the sequencing, the switch 30f closes to actuate the alarm circuit 14, which by way of specific embodiment may be a Milletron, Inc., Model BA-02 backup alarm. Actuation of the alarm circuit 14 causes the illumination of the "out alarm" lamp 110 and an audible warning signal from the speaker 111 through leads 112 and 113 in circuit with the switch 114 at the output of the alarm 14. When the alarm switch 114 is in the position shown, the alarm is at its loudest for in-plant testing. When the switch 114 is transferred to its middle position, the resistor 116, on the order of 150 ohms, is placed in series with the lead 113 to mute the audible signal from the speaker 111 for use, for example, in demonstrating the instrument in an office or other position where the loud alarm would be objectionable. By transferring the switch 114 to its third position, the alarm may be tested momentarily to verify that the alarm is working properly. The alarm 14 is energized by a connection of leads 116 and 117 to the leads 66 and 68 which energize the "probe ready" lamp 63 in the manner previously described.

As previously indicated, the apparatus according to the invention is operated from an a-c line voltage for the situation when it is convenient to plug the cord into a grounded 110 volt a-c recepticle by placing the power switch 41 in the a-c position shown. The apparatus can also be operated from a built-in power supply, designated generally by the reference numeral 125, which includes the batteries 67, and a d-c/a-c power inverter 126. The inverter 126 transforms the 12 volt input from the batteries 67 to 110 volt a-c output to operate the circuit in the manner previously described. The capacitor 130 is provided to filter the a-c components which may exist in the d-c signal at the input of the inverter 126.

A battery charger circuit is also provided which includes a battery charger 129 in circuit with the switch 45. When the switch 45 is closed, the power from the recepticle 40a is provided on the leads 130 and 131 to the battery charger 129 which is connected to the leads 132 and 133 in circuit with the batteries 67.

A testing circuit to determine whether the batteries 67 are in need of charging is also provided, as indicated by the reference numeral 135, comprising a pair of resistors 136 and 137 in parallel with the resistor 138 and in circuit with the switch 105, as shown.

With the closure of the switch 105, the rechargeable battery voltage is read directly on the digital panel meter 36 by dividing the 12 volt battery voltage down on the order of 1000 to 1 through the resistors 136 and 137. By way of a specific embodiment, resistor 136 is 47 ohms while resistor 137 is 47 K ohms and resistor 138 is 25 ohms. The resistor 131 is a dummy load applied only when the switch 105 is depressed to drop the open circuit battery voltage down to its true loaded voltage. This feature permits the operator to determine directly whether the battery needs to be recharged under simulated load conditions and to take appropriate action.

A calibrate signal circuit, designated generally by the reference numeral 86, comprises a switch 150 in circuit with leads 151 and 81. A zener diode 152 is in circuit with a plurality of resistors 153. This circuit permits the input signals to be calibrated. When the switch 150 is depressed, internal voltages are applied to the circuit. Holding the switch down until the alarm 14 operates will cause the instrument to run through its cycle and show calibration voltages on both the recorder 28 and on the panel meter 36. These readings are used to determine that the instrument is operating properly. During calibration, a probe 10 is not connected to the circuit because the thermocouple in the probe will short out the voltage applied to the meter 36 thereby causing an erroneous reading.

Finally, the switch 161 is a switch in circuit with the strip chart recorder, provided by the manufacturer, for causing the chart to be operated and is used, for example, to space the readings on the chart or to run the chart paper out from the recorder.

The invention may be embodied in other specific forms without departing from its spirit or essential characteristics. The present embodiments are, therefore, to be considered in all respects as illustrative and not restrictive, the scope of the invention being indicated, by the claims rather than by the foregoing description, and all changes which come within the meaning and range of the eqivalents of the claims are therefore intended to be embraced therein.

What is claimed is:

1. An apparatus for displaying at least a pair of physical representations which respectively represent at least a first and a second sensed parameter, comprising the combination of:

input circuit means for receiving a first signal and a second signal which are respectively electrical representations of said first parameter and said second parameter;

first recording means operatively connected to said input circuit means for receiving said first signal representative of said first parameter and for displaying a first physical representation of said signal upon command;

second recording means for receiving said second signal representative of said second parameter and for displaying a second physical representation of said second signal, said second recording means including limiting means responsive to a predetermined level of said second signal for initiating the operation of said second recording means;

sequencing means initially responsive to said limiting means for causing said first recording means to display said first representation of said first parameter; and a source of power operatively connected to said first recording means and said second recording means.

2. The apparatus as set forth in claim 1 wherein said sequencing means (a) operates in response to said limiting means and causes said sequencing means to be operatively connected to said source of power for a predetermined cycle and (b) then causes said first signal to be operatively connected from said input means to said first recording means so that said first recording means displays said first representation of said first signal.

3. The apparatus as set forth in claim 2 further including means responsive to said sequencing means for indicating a predetermined time in said predetermined cycle.

4. The apparatus as set forth in claim 2 wherein said input circuit means includes a low input resistance and said sequencing means further causes said low input resistance to be removed therefrom so that input circuit means has a high input resistance, said low input resistance being removed after said sequencing means is operatively connected to said source of power and before said first recording means displays said first signal.

5. The apparatus as set forth in claim 4 wherein said first recording means includes read and hold means for causing a physical representation on said first recording means to be retained until released by said sequencing means, said sequencing means causing a previous representation to be released prior to causing said first signal to be operatively connected to said first recording means.

6. The apparatus as set forth in claim 1 wherein said source of power includes means for providing power from either a conventional a-c source or from batteries, and means for switching therebetween.

7. The apparatus as set forth in claim 1 wherein said apparatus further includes means for charging said battery.

8. The apparatus as set forth in claim 7 wherein said apparatus further includes means for determining whether said battery needs charging.

9. The apparatus as set forth in claim 1 wherein said input circuit means further includes temperature measuring means for producing said first parameter and dissolved oxygen measuring means for producing said second parameter.

10. The apparatus as set forth in claim 9 in combination with a solid electrolyte sensor capable of being plunged into liquid metal comprising a small mass of solid oxygen-permeable electrolyte in a refractory insulating tube, an oxygen reference material in contact with said electrolyte and wherein said temperature measuring means includes a plurality of electrodes for providing an emf representative of the temperature of the probe and said dissolved oxygen measuring means includes a plurality of electrodes for providing an emf representative of the dissolved oxygen content of the metal, said electrodes being in circuit with said input circuit means.

11. The apparatus as set forth in claim 10 further including means for indicating whether said sensor is operatively connected to said apparatus.

12. The apparatus as set forth in claim 11 further including means for indicating when said sequencing means is operating, indicating that readings from said sensor are being obtained.

13. An apparatus for displaying a physical representation which represents a sensed parameter comprising:
input circuit means for receiving a signal wich is an electrical representative of said parameter;
recording means operatively connected to said input circuit means for receiving said signal and displaying a first physical representation of said signal, said recording means including limiting means responsive to a predetermined level of said signal; and
sequencing means initially responsive to said limiting means for causing said input circuit means to exhibit a high input impedance to said signal.

14. An apparatus as set forth in claim 13 wherein said sensed parameter is an emf representing the dissolved oxygen content of a liquid metal.

15. An apparatus as set forth in claim 14 in combination with a solid electrolyte sensor capable of being plunged into liquid metal comprising a small mass of solid oxygen-permeable electrolyte and a plurality of electrodes for providing an emf representative of the temperature of the probe and an emf representative of the dissolved oxygen content of the metal, said electrodes being in circuit with said input circuit means.

16. A method for displaying a first signal representing the temperature of a liquid metal, and a second signal representative of the dissolved oxygen content of the liquid metal, said first signal and said second signal being derived from a sensor capable of being plunged into the liquid metal and comprising a small mass of solid oxygen-permeable electrolyte in a refractory insulating tube, an oxygen reference material in contact with said electrolyte, and a plurality of electrodes for providing said first signal and said second signal, comprising the steps of:
plunging said probe into said liquid metal,
displaying a second physical representation of said second signal when said second signal reaches a predetermined level,
displaying a first physical representation of said first signal in response to said second signal reaching said predetermined level, and
indicating that said first physical representation and said second physical representation have been displayed.

17. The method as set forth in claim 16 further including the steps of:
causing a low input impedance to said second signal to be translated into a high input impedance prior to the step of displaying said first physical representation of said first signal.

18. The method as set forth in claim 17 further including the step of causing said first physical representation to be retained for a predetermined period of time.

19. The method as set forth in claim 18 further including the step of testing to determine whether said probe is operative.

* * * * *